United States Patent [19]

Stueben

[11] 4,192,952

[45] Mar. 11, 1980

[54] CUMENE OXIDATION USING 'ONIUM CATALYSTS

[75] Inventor: Kenneth C. Stueben, Bridgewater, N.J.

[73] Assignee: Union Carbide Corporation, New York, N.Y.

[21] Appl. No.: 958,694

[22] Filed: Nov. 8, 1978

[51] Int. Cl.² ............................................. C07C 179/04
[52] U.S. Cl. ................................................. 568/574
[58] Field of Search ............................... 568/574, 575

[56] References Cited

PUBLICATIONS

Yablokova et al., "Tr. po. Khim i Khim.", Technol. 4, 455, (1961).
Fuku, et al., "Bull. Chem. Soc.", Japan 41, 312, (1969).
Ohkubo, et al., "Bull. Chem. Soc.", Japan 42, 1800, 2200, (1969).
Ohkubo, et al., "Bull. Chem. Soc.", Japan 45, 1571, (1972).

Primary Examiner—Werren B. Lone
Attorney, Agent, or Firm—Francis M. Fazio

[57] ABSTRACT

Substituted ammonium halides are used as catalysts for the oxidation of cumene to cumene hydroperoxide. Their use significantly increases the rate of oxidation and overcomes the effects of phenol contamination.

6 Claims, No Drawings

CUMENE OXIDATION USING 'ONIUM CATALYSTS

BACKGROUND OF THE INVENTION

Phenol is a useful chemical compound employed in the manufacture of a wide variety of substances, such as aspirin, oil of wintergreen and plastics. The oxidation of cumene to cumene hydroperoxide is the first step in an important commercial phenol synthesis. Therefore any means for increasing the rate of oxidation of cumene to cumene hydroperoxide would be of considerable commercial interest due to the added phenol production one might achieve without the need for new capital investment.

In this regard, many compounds have been claimed to improve the rate and/or selectivity of the cumene oxidation. As examples of such compounds one can cite a host of substances such as calcium carbonate, amines, and carbonyl compounds. There are also reports that certain salts may be catalytically active in this reaction including amine salts, certain 'onium tetrafluoborates and triphenylsulfonium chloride. In many instances experimental details are not available concerning the use of these compounds. Generally, however, the use of from 1000 ppm to 10,000 ppm of catalyst has been required.

Such large amounts of catalyst are costly primarily due to the lost efficiency which results when unwanted reaction products are formed along with the cumene hydroperoxide. Much effort has been expended to discover a catalyst which can be used in much smaller concentration to oxidize cumene. One such catalyst, triphenylsulfonium chloride, has shown effective catalytic activity in concentrations of as low as 50 ppm. However the efficiency of the triphenylsulfonium chloride catalyzed reaction has remained poor.

The oxidation of cumene to cumene hydroperoxide, like many free radical reactions, is quite sensitive to the presence of foreign material. The accidental contamination of cumene by phenol in concentrations as low as 150 ppm leads to a severe decline in the rate of oxidation of cumene to cumene hydroperoxide. Consequently, a preliminary costly purification of the phenol contaminated cumene is usually carried out. A means of eliminating the purification step, overcoming the decrease in oxidation rate which results from the contamination of cumene by phenol, and of increasing the oxidation rate without such a large sacrifice of efficiency would be highly desirable.

SUMMARY OF THE INVENTION

It has now been found that certain hereinafter described substituted ammonium halides can be used as catalysts for the oxidation of cumene to cumene hydroperoxide. These highly effective catalysts can be used in low concentrations to achieve significant increases in oxidation rate without the large efficiency losses heretofore encountered. On an equal weight basis, these compounds provide increased rates of reaction at up to three fold decreases in efficiency losses than those obtained with the frequently quoted triphenylsulfonium chloride. The use of these compounds in the process of this invention also significantly overcomes the decrease in the oxidation rate which results from the contamination of cumene by phenol.

DESCRIPTION OF THE INVENTION

In the process of this invention, cumene, in contact with oxygen and a catalytic amount of a substituted ammonium halide, is oxidized to cumene hydroperoxide.

In the process of this invention, the concentration of cumene to be oxidized present in the reaction mixture can vary from 50 weight percent to 99.9 weight percent based on the total weight of the reaction mixture and it is preferably from 70 weight percent to 99.5 weight percent. Cumene hydroperoxide may also be present in the reaction mixture and the concentration of the cumene hydroperoxide can vary from about 0.1 weight percent to 50 weight percent preferably from about 0.1 weight percent to 30 weight percent based on the total weight of the reaction mixture. The presence of the peroxide as well as traces of phenol is due to the fact that the commercial process is a recycle process and no efforts are completely successful in removing these components.

The substituted ammonium halides used in the process of this invention are of the general formula:

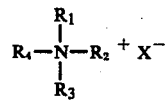

where X is a halide such as fluorine, chlorine, bromine and iodine; and where $R_1$, $R_2$ and $R_3$ taken singly can be:

(a) alkyl, linear or branched, substituted or unsubstituted, having from one to forty carbon atoms, preferably from one to twenty carbon atoms such as methyl, ethyl, isopropyl, hexadecyl, eicosyl, tetracontyl, and the like;

or (b) aryl, substituted or unsubstituted, such as tolyl, phenyl, xylyl, 2,4-dichlorophenyl, 4-chlorophenyl, and the like;

or (c) aralkyl, substituted or unsubstituted, having from seven to twenty carbon atoms such as benzyl, phenethyl, 4-methylbenzyl, and the like;

or (d) hydrogen;

and where $R_4$ can be:

(a) alkyl, linear or branched, substituted or unsubstituted, having from one to forty carbon atoms, preferably from one to twenty carbon atoms such as methyl, ethyl, isopropyl, hexadecyl, eicosyl, tetracontyl, and the like;

or (b) aryl, substituted or unsubstituted, such as tolyl, phenyl, xylyl, 2,4-dichlorophenyl, 4-chlorophenyl, and the like;

or (c) aralkyl, substituted or unsubstituted, having from seven to twenty carbon atoms such as benzyl, phenethyl, 4-methylbenzyl, and the like;

and where $R_2$, $R_3$ and $R_4$ taken together with the nitrogen atom can form a heterocyclic ring containing from four to eight ring carbon atoms such as imidazoyl, tetrahydropyrimidyl, pyridinium, and the like, which ring can have attached to it pendant alkyl chains of up to eighteen carbon atoms.

Illustrative of the quaternary ammonium halides suitable for use as catalysts in the process of this invention one can name lauryltrimethylammonium chloride, ethylhexadecyldimethylammonium bromide, hexadecyltrimethylammonium bromide, tetraethylammonium bromide, hexadecylpyridinium chloride, trioctylammonium hydrochloride, octylamine hydrochloride, ethylene diamine hydrochloride, 1,6-hexanediamine hydrochloride, N-ethyl aniline hydrochloride, 2,5-toluene diamine hydrochloride, lysine monohydrochloride and 2-amino-1-phenyl-1-propanol hydrochloride. One of the most preferred catalysts is lauryltrimethylammonium chloride.

The $R_1$, $R_2$, $R_3$ and $R_4$ groups can be unsubstituted or substituted with any substituent group which will not unduly interfere with the oxidation process of this invention. Thus, there can be present as substituent groups hydroxyl, ether linkages, halogens and others that would not interfere with the reaction.

The concentration of the catalyst can vary from 1 ppm to 900 ppm, preferably from 25 to 500 ppm, most preferably from 25 to 50 ppm, based on the total weight of the reaction mixture. Any catalytic amount sufficient to catalyze the reaction can be used. It was observed that increasing the concentration of the substituted ammonium halide catalyst substantially above 50 ppm had little effect upon the rate of cumene hydroperoxide formation and resulted in a lower reaction efficiency by contributing to the increased formation of by-products, such as acetophenone and dimethylphenylcarbinol, during the reaction.

The reaction can be carried out at a temperature of from about 85° C. to about 135° C., preferably from about 100° C. to about 120° C. The temperature used is that known to those skilled in the art. The rate of cumene hydroperoxide formation increases as the reaction temperature increases but the efficiency of the reaction decreases due to the increase in formation of by-products, such as acetophenone and dimethylphenylcarbinol.

The time required for a particular reaction will vary and is dependent upon the concentration and purity of the initial reactants, the type and concentration of the catalyst, the temperature, the airflow, the agitation, and the size of the batch.

In a typical embodiment, 360 grams of a mixture of about 95 weight percent cumene, about 5 weight percent cumene hydroperoxide and 50 ppm lauryltrimethylammonium chloride was charged to a glass reactor. The temperature of the mixture was raised to 110° C. and the airflow was started. The temperature was maintained at from 108° C. to 112° C. and airflow was maintained at from 490 ml per minute to 510 ml per minute while the reaction proceeded for 3.6 hours. At completion, a sample of the mixture was analyzed for cumene hydroperoxide concentration using the sodium thiosulfate method.

After the reaction proceeds for a period of time sufficient to allow the cumene hydroperoxide concentration to increase to about 30 weight percent based on the total weight of the mixture, the mixture is subjected to vacuum distillation and the concentration of cumene hydroperoxide is increased to about 80 weight percent. This concentrated mixture is then mixed with an acid catalyst to decompose the cumene hydroperoxide to phenol and acetone.

Cumene hydroperoxide, the product of the process of the invention, is an intermediate in the commercial synthesis of phenol. Phenol is used in the manufacture of many substances among which are phenolic resins, epoxy resins, aspirin, oil of wintergreen and weed killers.

It was completely unexpected and unobvious to find that the use of such small amounts of substituted ammonium halides in the oxidation of cumene would result in such an increase in the rate of formation of cumene hydroperoxide and also overcome the deleterious effects caused by the contamination of cumene with phenol, which is a fairly common occurrence in commercial phenol production from cumene.

In Experiments A, B, and C, the oxidation reaction was carried out by the procedures commonly employed today. These experiments are presented for comparison with the results reported in the examples that were obtained by the new catalytic process of this invention.

EXPERIMENT A

There was charged to a glass reactor 360 grams of a mixture of 95.28 weight percent cumene and 4.72 weight percent cumene hydroperoxide. The reactor was equipped with a thermometer, a gas inlet tube, a sample removal tube, a stirrer and an exhaust system. Compressed air passed successively through a reducing valve, a container of glass wool, a flowmeter and finally entered the gas inlet tube and a fritted disc sparger of medium porosity located just below the stirrer. The temperature of the mixture was raised to 110° C. and the airflow was started; it was maintained at 110° C. by immersing the lower portion of the reactor in a thermostated oil bath. The airflow was maintained at from 490 ml per minute to 510 ml per minute and the stirrer speed was set at 120 rpm and monitored by a phototachometer. One gram samples were analyzed for cumene hydroperoxide content by the addition of the accurately weighed sample of 50 ml of isopropanol, 10 ml of glacial acetic acid and 10 ml of a 50 percent by volume potassium iodide solution, followed by swirling, immersing in a steam bath for ten minutes and titrating while hot with a 0.1 N sodium thiosulfate solution. The cumene hydroperoxide concentration was calculated using the following equation:

$$\% \text{ CHP} = \frac{(\text{ml of titer}) (\text{normality Na}_2\text{S}_2\text{O}_3) (.0761) (100)}{(\text{weight sample in grams})}$$

After 5.6 hours of reaction, the analysis showed a cumene hydroperoxide content of 28.88 weight percent indicating a rate of formation of cumene hydroperoxide of 4.3 weight percent per hour.

EXPERIMENT B

There was charged to the apparatus described in Experiment A, 360 grams of a mixture of 94.81 weight percent cumene, 5.03 weight percent cumene hydroperoxide and trace amounts of acetophenone and dimethylphenylcarbinol. To the mixture there was added 150 ppm of phenol as an impurity. The experiment and analysis were conducted using procedures and conditions similar to those described in Experiment A. After 6.0 hours of reaction the analysis showed a cumene hydroperoxide content of 22.43 weight percent indicating a rate of formation of cumene hydroperoxide of 2.9 weight percent per hour. This experiment, when compared to the results shown in Experiment A, shows that contamination of cumene with as little as 150 ppm of phenol can reduce the rate of formation of cumene hydroperoxide by about 33 percent.

EXPERIMENT C

There was charged to the apparatus described in Experiment A, 360 grams of a mixture of 95.51 weight percent cumene, 3.77 weight percent cumene hydroperoxide, and trace amounts of acetophenone and dimethylphenylcarbinol. To this mixture was added 50 ppm of triphenylsulfonium chloride as catalyst. The experiment was conducted using procedures and conditions similar to those described in Experiment A. The efficiency of the reaction was calculated using the following formula:

$$EFF = \frac{\Delta \text{ moles CHP} \times 100}{\Delta (\text{moles CHP} + \text{moles DMPC} + \text{moles ACP})}$$

Comparison with Experiment A showed a loss of efficiency of 6.4 percent. This Experiment illustrates the loss of efficiency which results when the reaction is catalyzed using one of the most frequently reported catalysts.

The following examples serve to further illustrate the invention.

EXAMPLE 1

There was charged to a glass reactor 360 grams of a mixture of 94.50 weight percent cumene, 5.37 weight percent cumene hydroperoxide and trace amounts of acetophenone and dimethylphenylcarbinol. To this mixture was added 50 ppm of lauryltrimethylammonium chloride as catalyst. The reactor was equipped with a thermometer, a gas inlet tube, a sample removal tube, a stirrer and an exhaust system. Compressed air was introduced as described in Experiment A and the mixture reacted at 110° C. At intervals one gram samples were removed and analyzed for cumene hydroperoxide content. After 3.6 hours of reaction, the analysis showed a cumene hydroperoxide content of 30.48 weight percent, indicating a rate of formation of cumene hydroperoxide of 6.9 weight percent per hour. Comparison with Experiment A shows that the addition of as little as 50 ppm of lauryltrimethylammonium chloride to cumene can increase the rate of cumene hydroperoxide formation by about 60 percent over the rate achieved during the uncatalyzed reaction. The efficiency of the reaction was calculated using the formula of Experiment C. Comparison with Experiment A showed a loss of efficiency of only 2.3 percent as compared to the 6.4 percent efficiency loss found in Experiment C when the reaction was catalyzed with triphenylsulphonium chloride. This Example illustrates that efficiency losses using the catalysts of this invention are reduced by 64 percent over those efficiency losses encountered when the reaction is catalyzed with similar amounts of one of the most commonly cited catalysts.

EXAMPLE 2

There was charged to the apparatus described in Example 1, 360 grams of a mixture of 94.81 weight percent cumene, 5.03 weight percent cumene hydroperoxide and trace amounts of acetophenone and dimethylphenylcarbinol. To this mixture was added 150 ppm of phenol as an impurity and 50 ppm of lauryltrimethylammonium chloride as catalyst. The experiment and analysis were conducted using procedures and conditions similar to those used in Example 1. After only 4.5 hours of reaction, the analysis showed a cumene hydroperoxide content of 29.93 weight percent indicating a rate of formation of cumene hydroperoxide of 5.6 weight percent per hour. Comparison with Experiment B shows that the addition of as little as 50 ppm of lauryltrimethylammonium chloride overcomes the deleterious effect of phenol contamination of cumene; comparison with Experiment A shows that it leads to even better results than obtained during an uncatalyzed, uncontaminated oxidation. The rate of cumene hydroperoxide formation was about 93 percent greater than the rate achieved during the phenol-contaminated and uncatalyzed oxidation reaction in Experiment B and about 30 percent greater than the rate achieved during the uncontaminated and uncatalyzed oxidation reaction in Experiment A.

EXAMPLE 3

There was charged to the apparatus described in Example 1, 360 grams of a mixture of 94.81 weight percent cumene, 5.03 weight percent cumene hydroperoxide and trace amounts of acetophenone and dimethylphenylcarbinol. To this mixture was added 55 ppm of phenol as an impurity and 50 ppm of lauryltrimethylammonium chloride as catalyst. The experiment and analysis were conducted using procedures and conditions similar to those used in Example 1. After only 3.8 hours of reaction, the analysis showed a cumene hydroperoxide content of 29.92 weight percent indicating a rate of formation of cumene hydroperoxide of 6.6 percent per hour. The rate of cumene hydroperoxide formation was about 128 percent greater than the rate achieved during the phenol-contaminated and uncatalyzed oxidation reaction in Experiment B.

EXAMPLE 4

There was charged to the apparatus described in Example 1, 1800 grams of a mixture of 94.85 weight percent cumene, 4.63 weight percent cumene hydroperoxide and trace amounts of acetophenone and dimethylphenylcarbinol. To this mixture was added 100 ppm of lauryltrimethylammonium chloride as catalyst. The experiment and analysis were conducted using procedures and conditions similar to those used in Example 1 except that the airflow was maintained at from 1475 ml per minute to 1525 ml per minute and the stirrer speed was set at 1675 rpm. After 2.5 hours of reaction, the analysis showed a cumene hydroperoxide content of 19.33 weight percent indicating a rate of formation of cumene hydroperoxide of 6.0 weight percent per hour. The rate of cumene hydroperoxide formation was about 40 percent greater than the rate achieved during the uncatalyzed oxidation reaction in Experiment A.

EXAMPLE 5

There was charged to the apparatus described in Example 1, 1800 grams of a mixture of 94.54 weight percent cumene, 4.99 weight percent cumene hydroperoxide and trace amounts of acetophenone and dimethylphenylcarbinol. To this mixture was added 25 ppm of lauryltrimethylammonium chloride as catalyst. The experiment and analysis were conducted using procedures and conditions similar to those used in Example 4. After 3.0 hours of reaction, the analysis showed a cumene hydroperoxide content of 18.96 weight percent indicating a rate of formation of cumene hydroperoxide of 4.8 weight percent per hour. The rate of cumene hydroperoxide formation was about 12 percent greater than the rate achieved during the uncatalyzed oxidation reaction in Experiment A.

EXAMPLE 6

There was charged to the apparatus described in Example 1, 1800 grams of a mixture of 94.48 weight percent cumene, 2.81 weight percent cumene hydroperoxide and trace amounts of acetophenone and dimethylphenylcarbinol. To this mixture was added 500 ppm of lauryltrimethylammonium chloride as catalyst. The experiment and analysis were conducted using procedures and conditions similar to those used in Example 4. After 2.5 hours of reaction, the analysis showed a cumene hydroperoxide content of 18.78 weight percent indicating a rate of formation of cumene hydroperoxide of 6.6 weight percent per hour. The rate of cumene hydroperoxide formation was about 53 percent greater than the rate achieved during the uncatalyzed oxidation reaction in Experiment A.

EXAMPLE 7

There was charged to the apparatus described in Example 1, 1800 grams of a mixture of 94.31 weight percent cumene, 5.10 weight percent cumene hydroperoxide and trace amounts of acetophenone and dimethylphenylcarbinol. To this mixture was added 50 ppm of ethylhexadecyldimethylammonium bromide as catalyst. The experiment and analysis were conducted using procedures and conditions similar to those used in Example 4. After 2.75 hours of reaction the analysis showed a cumene hydroperoxide content of 19.44 weight percent indicating a rate of formation of cumene hydroperoxide of 5.5 weight percent per hour. The rate of cumene hydroperoxide formation was about 28 percent greater than the rate achieved during the uncatalyzed oxidation reaction in Experiment A.

EXAMPLE 8

There was charged to the apparatus described in Example 1, 1800 grams of a mixture of 94.52 weight percent cumene, 4.95 weight percent cumene hydroperoxide and trace amounts of acetophenone and dimethylphenylcarbinol. To this mixture was added 50 ppm of hexadecyltrimethylammonium bromide as catalyst. The experiment and analysis were conducted using procedures and conditions similar to those used in Example 4. After 2.5 hours of reaction, the analysis showed a cumene hydroperoxide content of 19.55 indicating a rate of formation of cumene hydroperoxide of 5.6 weight percent per hour. The rate of cumene hydroperoxide formation was about 30 percent greater than the rate achieved during the uncatalyzed oxidation reaction in Experiment A.

EXAMPLE 9

There was charged to the apparatus described in Example 1, 1800 grams of a mixture of 94.32 weight percent cumene, 5.10 weight percent cumene hydroperoxide and trace amounts of acetophenone and dimethylphenylcarbinol. To this mixture was added 50 ppm of tetraethylammonium bromide as catalyst. The experiment and analysis were conducted using procedures and conditions similar to those used in Example 4. After 2.5 hours of reaction, the analysis showed a cumene hydroperoxide content of 19.97 weight percent indicating a rate of formation of cumene hydroperoxide of 6.1 weight percent per hour. The rate of cumene hydroperoxide formation was about 42 percent greater than the rate achieved during the uncatalyzed oxidation reaction in Experiment A.

What is claimed is:

1. A process for the production of cumene hydroperoxide which comprises the oxidation at from about 85° C. to about 135° C. of cumene in contact with oxygen and from 1 ppm to 900 ppm based on the total weight of the reaction mixture of a substituted ammonium halide catalyst of the general formula:

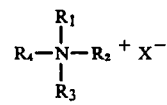

where X is a halide and where $R_1$, $R_2$ and $R_3$ taken singly can be:
   (a) alkyl, linear or branched, substituted or unsubstituted, having from one to forty carbon atoms; or
   (b) aryl, substituted or unsubstituted; or
   (c) aralkyl, substituted or unsubstituted, having from seven to twenty carbon atoms; or
   (d) hydrogen;
and where $R_4$ can be:
   (a) alkyl, linear or branched, substituted or unsubstituted, having from one to forty carbon atoms: or
   (b) aryl, substituted or unsubstituted; or
   (c) aralkyl, substituted or unsubstituted, having from seven to twenty carbon atoms; and where $R_2$, $R_3$ and $R_4$ taken together with the nitrogen atom can form a heterocyclic ring containing from four to eight ring carbon atoms.

2. A process as claimed in claim 1 wherein said catalyst is lauryltrimethylammonium chloride.

3. A process as claimed in claim 1 wherein said catalyst is ethylhexadecyldimethylammonium bromide.

4. A process as claimed in claim 1 wherein said catalyst is hexadecyltrimethylammonium bromide.

5. A process as claimed in claim 1 wherein said catalyst is tetraethylammonium bromide.

6. A process as claimed in claim 1 wherein the concentration of catalyst is from 25 ppm to 500 ppm based on the total weight of the reaction mixture.

* * * * *